US010549061B2

(12) United States Patent
Matula, Jr. et al.

(10) Patent No.: US 10,549,061 B2
(45) Date of Patent: Feb. 4, 2020

(54) PATIENT INTERFACE DEVICE HAVING CAM WHEEL ADJUSTMENT MECHANISM

(71) Applicant: KONINKLIJKE PHILIPS N.V., Eindhoven (NL)

(72) Inventors: Jerome Matula, Jr., Apollo, PA (US); Derrick Blake Andrews, Markleton, PA (US); Eugene N. Scarberry, Trafford, PA (US); Marcel Douglas Jaffre, Greensburg, PA (US); Anthony Startare, Belle Vernon, PA (US)

(73) Assignee: Koninklijke Philips N.V., Eindhoven (NL)

( * ) Notice: Subject to any disclaimer, the term of this patent is extended or adjusted under 35 U.S.C. 154(b) by 281 days.

(21) Appl. No.: 15/793,176

(22) Filed: Oct. 25, 2017

(65) Prior Publication Data
US 2018/0043127 A1   Feb. 15, 2018

Related U.S. Application Data

(62) Division of application No. 14/282,555, filed on May 20, 2014, now Pat. No. 9,821,133, which is a division
(Continued)

(51) Int. Cl.
*A61M 16/08* (2006.01)
*A61M 16/06* (2006.01)

(52) U.S. Cl.
CPC ........ *A61M 16/0816* (2013.01); *A61M 16/06* (2013.01); *A61M 16/0605* (2014.02);
(Continued)

(58) Field of Classification Search
CPC .... A61M 16/06–0694; A61M 16/0816; A62B 18/02; A62B 18/025; A62B 18/06; A62B 18/084
See application file for complete search history.

(56) References Cited

U.S. PATENT DOCUMENTS

| 4,498,471 A | 2/1985 | Kranz |
| 7,546,837 B2 | 6/2009 | Busch |

(Continued)

FOREIGN PATENT DOCUMENTS

| CN | 101455871 A | 6/2009 |
| JP | 2009039528 A | 2/2009 |

(Continued)

*Primary Examiner* — Valerie L Woodward
(74) *Attorney, Agent, or Firm* — Michael W. Haas

(57) ABSTRACT

A patient interface device includes a cushion member having a main body portion having a surface structured to engage a face of a patient. A frame member is coupled to the cushion member, and a fluid coupling conduit is coupled to the frame member. An engagement member is coupled to the cushion member; and a rotatable cam wheel is disposed between the frame member and the engagement member. Rotation of the cam wheel changes a position of the main body portion relative to the frame member. The cushion member includes a flexible portion adjacent the main body portion, and the cam wheel is rotatable about the flexible portion, such that rotation of the cam wheel about the flexible portion causes the flexible portion to deflect thereby moving the cushion member relative to the frame member.

14 Claims, 15 Drawing Sheets

Related U.S. Application Data of application No. 13/320,796, filed as application No. PCT/IB2011/050608 on Feb. 14, 2011, now Pat. No. 8,746,249.

(60) Provisional application No. 61/309,914, filed on Mar. 3, 2010.

(52) U.S. Cl.
CPC ...... *A61M 16/065* (2014.02); *A61M 16/0611* (2014.02); *A61M 16/0638* (2014.02); *A61M 16/0683* (2013.01); *A61M 16/0644* (2014.02)

(56) References Cited

U.S. PATENT DOCUMENTS

| | | | |
|---|---|---|---|
| 9,962,510 B2 | 5/2018 | Kranzng | |
| 2006/0118117 A1* | 6/2006 | Berthon-Jones | A61M 16/06 128/206.21 |
| 2006/0213521 A1 | 9/2006 | Radney | |
| 2007/0062537 A1 | 3/2007 | Chiesa | |
| 2008/0066761 A1 | 3/2008 | Hodos | |
| 2012/0080035 A1* | 4/2012 | Guney | A61M 16/06 128/205.25 |

FOREIGN PATENT DOCUMENTS

| | | |
|---|---|---|
| WO | WO2003035156 A2 | 5/2003 |
| WO | 2005018523 A2 | 3/2005 |
| WO | WO2006074517 A1 | 7/2006 |
| WO | WO2007021777 A2 | 2/2007 |
| WO | WO2007048174 A1 | 5/2007 |
| WO | WO2007084905 A2 | 7/2007 |
| WO | WO2007084905 A3 | 7/2007 |

\* cited by examiner

PATIENT INTERFACE DEVICE HAVING CAM WHEEL ADJUSTMENT MECHANISM

CROSS-REFERENCE TO RELATED APPLICATIONS

This application is a Divisional under 35 U.S.C. § 120 of U.S. patent application Ser. No. 14/282,555, filed May 20, 2014, which is a Divisional under 35 U.S.C. § 120 of U.S. patent application Ser. No. 13/320,796, filed Nov. 16, 2011, now U.S. Pat. No. 8,746,249, granted Jun. 10, 2014 which claims the priority benefit under 35 U.S.C. §119(e) of U.S. Provisional Application No. 61/309,914, filed on Mar. 3, 2010, the contents of which are herein incorporated by reference.

BACKGROUND OF THE INVENTION

1. Field of the Invention

The present invention relates to patient interface devices for transporting a gas to and/or from an airway of a user, and, in particular, to a patient interface device including a cam wheel adjustment mechanism for dynamically adjusting a component of the patient interface device, such as a mask, cushion, or forehead support.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. A number of different adjustment mechanisms for adjusting a component, such as a mask, of a patient interface device are known, including adjustment mechanisms that are based on sliding members, screw mechanisms, and pivoting arms, among others. However, all of these known mechanisms are based on a linear adjustment theory, and thus have a range of motion that goes either inward or outward with respect to the patient's face. There is thus room for improvement in the area of patient interface device adjustment mechanisms.

SUMMARY OF THE INVENTION

In one embodiment, a patient interface device is provided that includes a support structure, a pivot arm pivotably coupled to the support structure and structured to pivot about an axis, a patient coupling member, such as a mask, cushion, or a forehead support, coupled to the pivot arm, and a cam wheel rotateably coupled to the support structure and engaging the pivot arm, wherein rotation of the cam wheel relative to the support structure and the pivot arm causes the pivot arm to pivot about the axis and the patient coupling member to move either forward or backward along a path of movement.

In one exemplary embodiment, a patient interface device is provided that includes a support structure forming part of a headgear of the patient interface device, the support structure having a post portion having a first arm having a first aperture and a second arm having a second aperture, a pivot arm conduit pivotably coupled to the post portion and structured to pivot about an axis, wherein the pivot arm conduit has a first post rotateably received with the first aperture and a second post rotateably received with the first aperture, a patient coupling member, such as a mask, fluidly coupled to the pivot arm conduit, and a cam wheel rotateably coupled to the support structure and engaging the pivot arm, wherein the post portion of the support structure is received through the cam wheel and the cam wheel is positioned between a base portion of the support structure and the pivot arm conduit, and wherein rotation of the cam wheel relative to the support structure and the pivot arm conduit causes the pivot arm conduit to pivot about the axis and the patient coupling member to move either forward or backward along a path of movement.

In another exemplary embodiment, a patient interface device is provided that includes a support structure having a post portion having a first post and a second post extending therefrom, a patient coupling member, such as a mask, fluidly coupled to the support structure, a pivot arm conduit pivotably coupled to the post portion and structured to pivot about an axis, wherein a first end of the pivot arm includes a loop portion having a first aperture and a second aperture provided therein, wherein the post portion is received through the loop portion, wherein the first post is rotateably received within the first aperture and the second post is rotateably received within the second aperture, a forehead support coupled to a second end of the pivot arm, and a cam wheel rotateably coupled to the support structure and engaging the pivot arm, wherein the cam wheel is positioned between a base portion of the support structure and the loop portion, and wherein rotation of the cam wheel relative to the support structure and the pivot arm causes the pivot arm to pivot about the axis and the forehead support to move either forward or backward along a path of movement.

In an alternative embodiment, a patient interface device is provided that includes a cushion member having a main body portion having a surface structured to engage the face of a patient, a frame member coupled to the cushion member, the frame member being structured to be coupled to a headgear, a fluid coupling conduit coupled to a first side of the frame member, an engagement member coupled to the cushion member, and a rotatable cam wheel disposed between a second side of the frame member and the engagement member, wherein a first surface of the cam wheel engages the engagement member such that rotation of the cam wheel relative to the cushion member changes a position of the main body portion relative to the frame member.

In yet another embodiment, a patient interface device is provided that includes a cushion member having a main body portion having a surface structured to engage a face of a patient, a frame member coupled to the cushion member, the frame member being structured to be coupled to a headgear, a fluid coupling conduit coupled to a first side of the frame member, one or more first magnets coupled to the cushion member, the one or more first magnets having a first polarity, and a rotatable cam wheel disposed between a second side of the frame member and the one or more first magnets. The cam wheel includes one or more second magnets facing toward the one or more first magnets and having a second polarity opposite the first polarity, wherein rotation of the cam wheel relative to the cushion member changes a position of the main body portion relative to the frame member as a result of opposing forces between the one or more first magnets and one or more of the plurality of second magnets.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
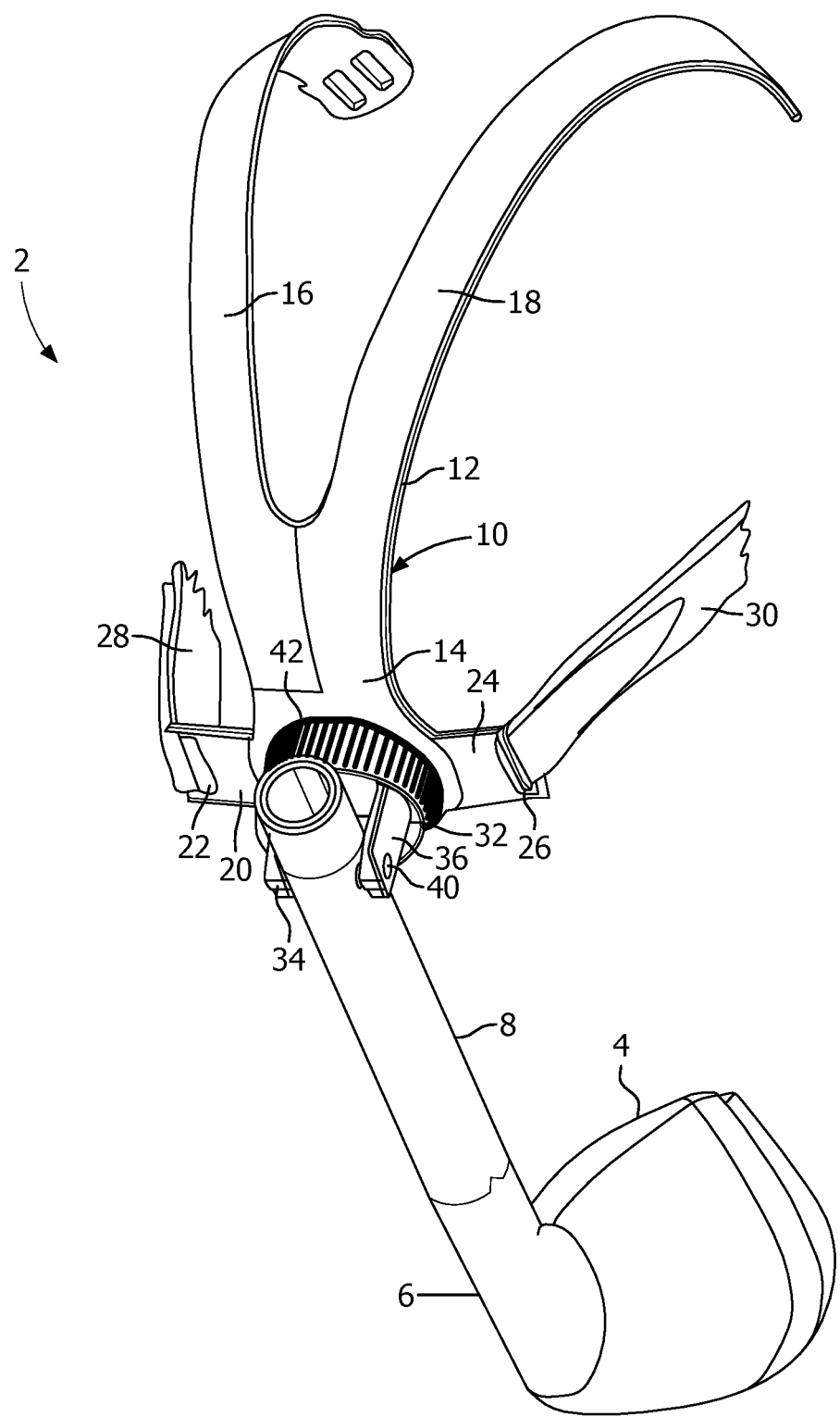
FIG. 1 is an isometric view of a patient interface device according to one exemplary embodiment of the present invention.
Figure 2:
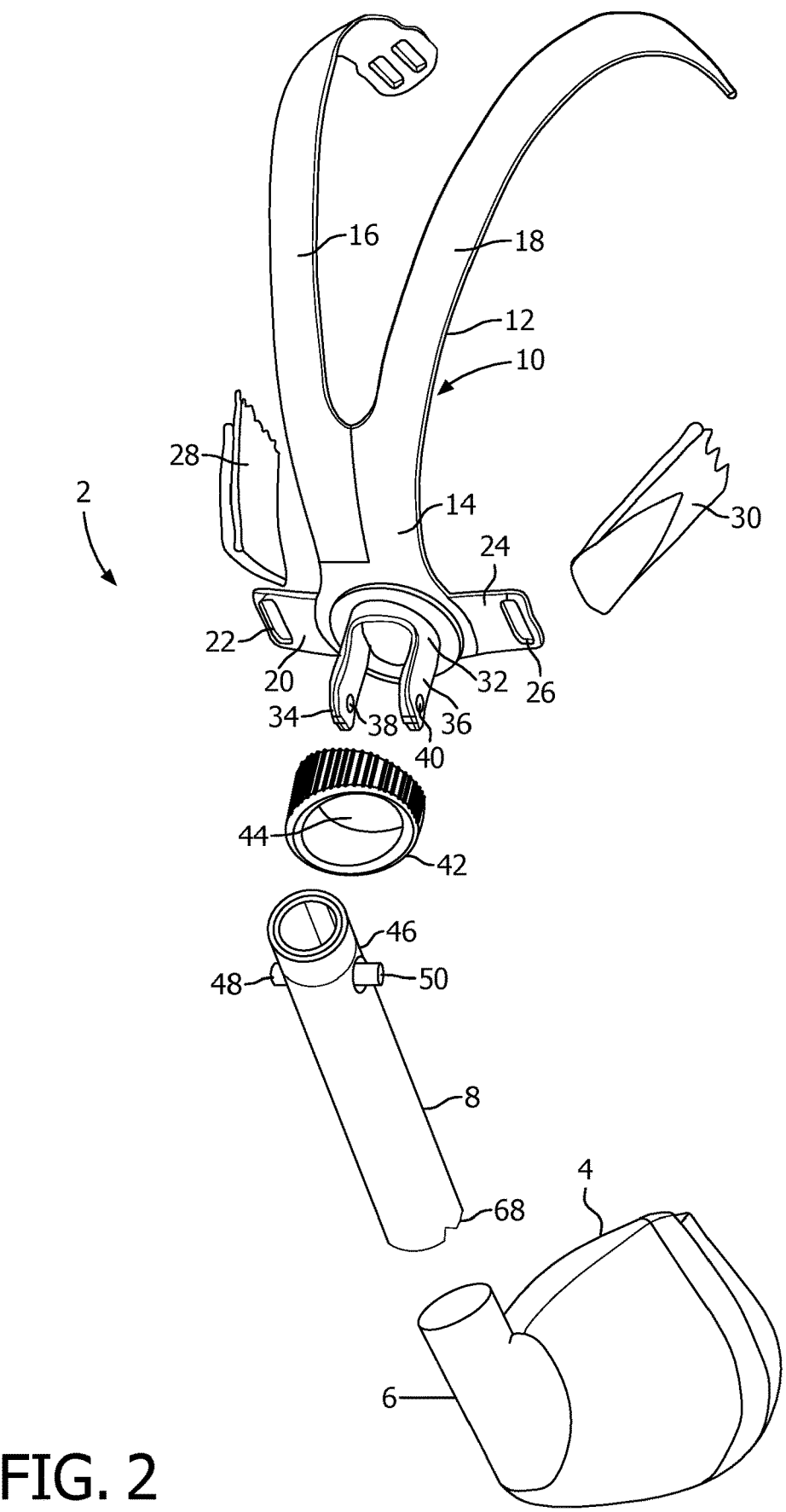
FIG. 2 is an exploded view of the patient interface device of FIG. 1.
Figure 3A:
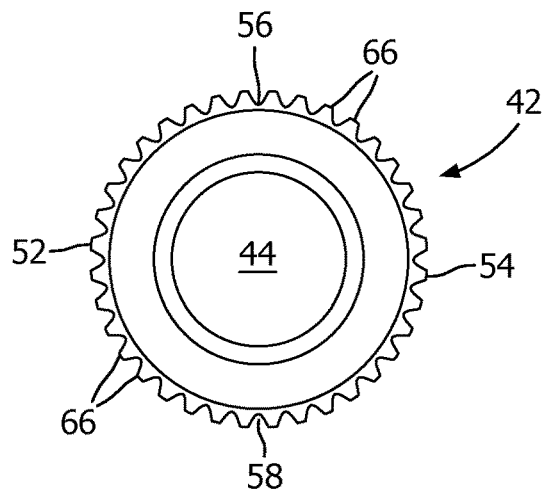
FIGS. 3A-3E are top plan, bottom plan, right side elevational, top side elevational, and isometric views, respectively, of a cam wheel forming part of the patient interface device of FIGS. 1 and 2.
Figure 3B:
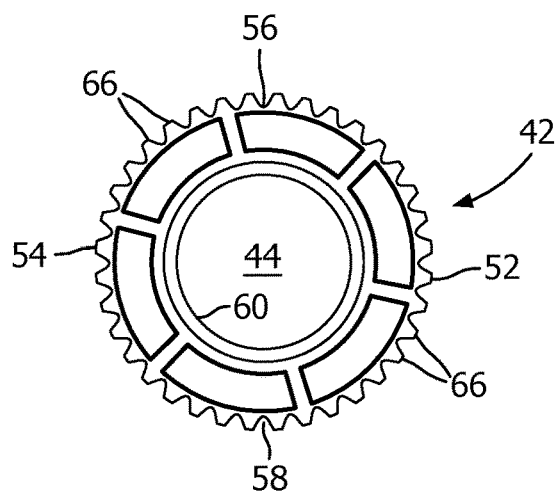
Figure 3C:
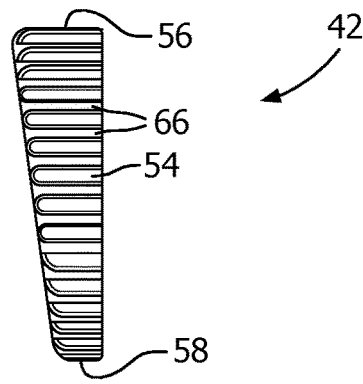
Figure 3D:
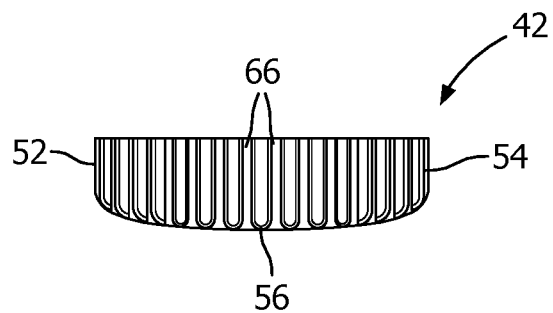
Figure 3E:
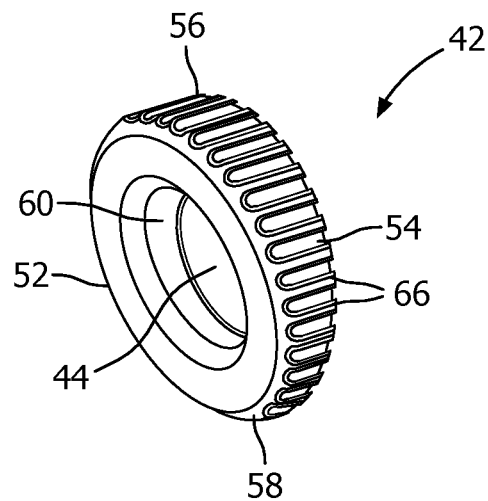

FIG. 1 is an isometric view and FIG. 2 is an exploded view of a patient interface device 2 according to one exemplary embodiment of the present invention. Patient interface device 2 includes a patient coupling member 4, which in the illustrated embodiment is a nasal mask. However, any type of patient sealing element or other mechanism for communicating a flow of gas with an airway of a user, such as a nasal/oral mask, a full face mask, nasal cannula, that facilitates the delivery of a flow of breathing gas to the airway of a patient, may be used as patient coupling member 4 while remaining within the scope of the present invention. Patient coupling member 4 is coupled to elbow conduit 6, which, in turn, is coupled to pivot arm conduit 8. Pivot arm conduit 8 is structured to be coupled to a delivery conduit (not shown) which is in fluid communication with a pressure generating device (also not shown) that is structured to generate a flow of breathing gas which is delivered to the patient through patient coupling member 4.

The pressure generating device may include, without limitation, a ventilator, constant pressure support device (such as a continuous positive airway pressure device, or CPAP device), a variable pressure support device (e.g., BIPAP®, Bi-Flex®, or C-Flex™ devices manufactured and distributed by Philips Respironics of Murrysville, Pa.), or an auto-titration pressure support device. In one exemplary embodiment, the delivery conduit that is coupled to pivot arm conduit 8 is adapted to extend over the patient's head when a headgear assembly 10 of patient interface device 2, described below, is worn on the head of the patient.

As noted above, patient interface device 2 includes a headgear assembly 10 adapted to fit over/around the patient's head to hold patient coupling member 4 in place on the face of the patient. Headgear assembly 10 includes a rigid support structure 12 adapted to fit over the forehead, top and rear portions of the patient's head. Support structure 12 includes a base portion 14 having arms 16, 18 extending therefrom. In addition, base portion 14 has an extension member 20 extending from a first side thereof and an extension member 24 extending from a second side thereof. Each extension member 20, 24 includes a respective loop 22, 26, which is structured to receive a respective headgear strap 28, 30 of headgear assembly 10 for securing headgear assembly 10 and thus patient interface device 2 to the head of the patient.

Base portion 14 of support structure 12 further includes a post portion 32 extending from a front face thereof. Post portion 32 includes a post arm 34 having aperture 38 formed therein, and a post arm 36 having an aperture 40 formed therein. Patent interface device 2 also includes a cam wheel 42 that is described in greater detail below in connection with FIGS. 3A-3E, which are top plan, bottom plan, right side elevational, top side elevational, and isomeric views, respectively, of the cam wheel. Cam wheel 42 includes central bore 44.

As seen in FIG. 1, when patient interface device 2 is assembled, cam wheel 42 is placed over post portion 32 in a manner in which post arms 34, 36 of post portion 32 are received through central bore 44 of cam wheel 42. Cam wheel 42 is free to rotate about post portion 32. In addition, as seen in FIG. 2, the top end 46 of pivot arm conduit 8 includes posts 48, 50 on opposite sides thereof. As seen in FIG. 1, when patient interface device 2 is assembled, each post 48, 50 of pivot arm conduit 8 is rotateably received and held within a respective aperture 38, 40 of base portion 14. Pivot arm conduit 8, when so mounted to base portion 32, secure and holds cam wheel 42 in place between pivot arm conduit 8 and base portion 14. In addition, as seen in FIG. 1, pivot arm conduit 8 will always contact cam wheel 42 in two places as cam wheel 42 is rotated about post portion 32.

Referring to FIGS. 3A-3E, in an exemplary embodiment, cam wheel 42 is a cylindrically shaped member having left and right outside walls 52, 54 that vary in height from a maximum at top middle portion 56 of cam wheel 42 to a minimum at bottom middle portion 58 of cam wheel 42. More particularly, in the illustrated embodiment, the height of each of left outside wall 52 and right outside wall 54 tapers and decreases linearly from top middle portion 56 to bottom middle portion 58. Left and right outside walls 52, 54 are provided with ridges 66 to facilitate gripping and turning of cam wheel 42 as described elsewhere herein. While an generally linear change in height for the wall of the cam wheel is shown, it is to be understood that the present invention contemplates that the wall of the cam wheel can have other shapes or changes in height.

As noted above, pivot arm conduit 8 will always contact cam wheel 42 in two places as cam wheel 42 is rotated about post portion 32. Thus, in operation, when a patient dons patient interface device 2, patient coupling member 4 will engage the patient's face. As the patient selectively rotates cam wheel 42 about post portion 32, the varying height of the walls of cam wheel 42 as defined by left and right outside walls 52, 54 and the two points of contact between cam wheel 42 and pivot arm conduit 8 described above will cause pivot arm conduit 8 to pivot about the axis through pivot arm conduit 8 that is defined by posts 48, 50. Such pivoting causes bottom end 68 of pivot arm conduit 8, and thus patient coupling member 4 attached thereto, to move inwardly and outwardly along a defined path of movement in a corresponding fashion.

Stated another way, rotation of cam wheel 42 results in movement of patient coupling member 4 relative to support structure 12. In this embodiment, support structure 12 is fixed on the user's head. As a result, when the cam wheel is actuated the patient coupling member moves toward or away from the user's face, thus adjusting the force of the seal provided by the patient coupling member against the face of the user.

Pivot arm conduit 8, post portion 32, and cam wheel 42, as just described, thus provides an easy to use, reduced complexity adjustment mechanism for patient interface device 2. Because cam wheel 42 is able to be turned both clockwise and counter clockwise, the position of patient coupling member 4 can be readily and easily adjusted both inwardly and outwardly relative to the patient's airway when the patient interface device is worn by the user. Furthermore, as the outer diameter of cam wheel 42 is made larger, it becomes easier to use by people with less strength and/or dexterity in their hands, such as the elderly.

Figure 4:
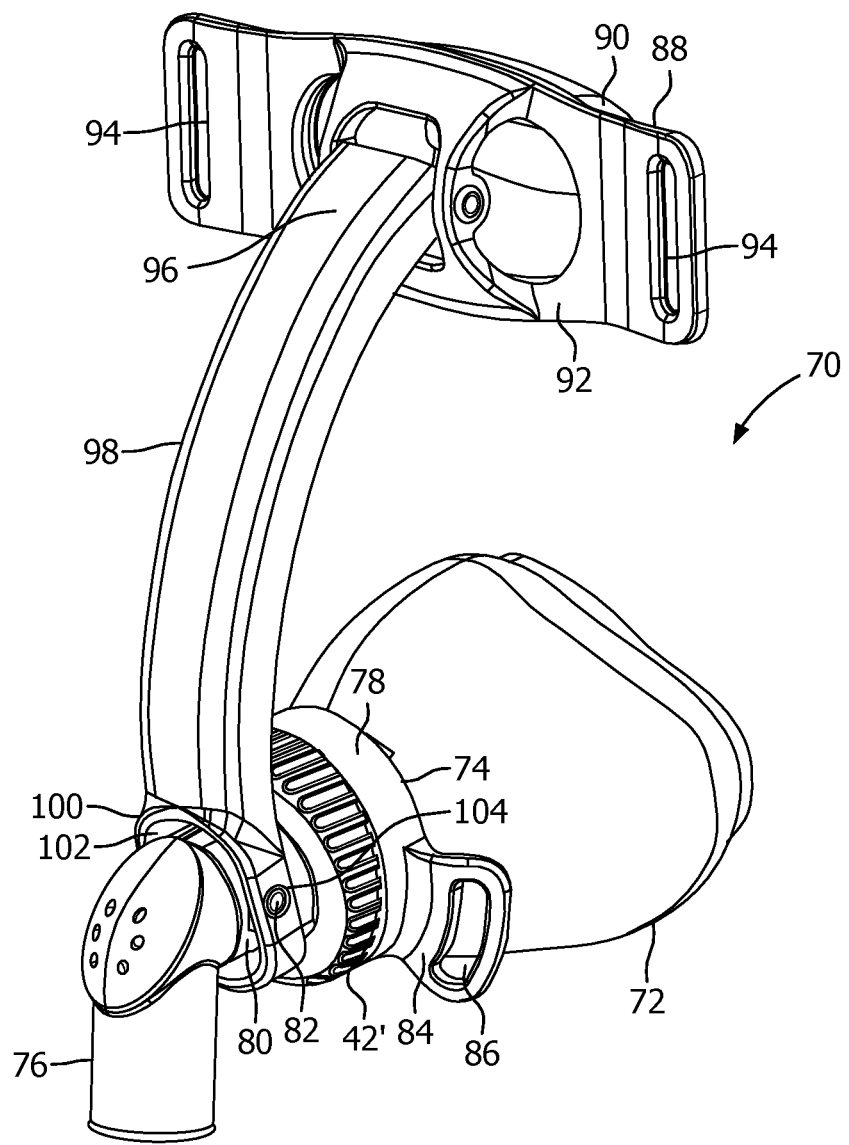
FIG. 4 is an isometric view of a patient interface device according to an alternative exemplary embodiment of the present invention.

FIG. 4 is an isometric view of a patient interface device 70 according to an alternative exemplary embodiment of the present invention. Patient interface device 70 includes patient coupling member 72 that, like in the previous embodiment, is also a patient sealing element that seals an airway of the user. In this illustrated exemplary embodiment, the patient sealing element is a nasal mask that includes a cushion that contacts the face of the user. However, any type of patient coupling member, such as a nasal/oral mask, nasal cannula or a full face mask, which facilitates the delivery of a flow of breathing gas to the airway of a patient, may be used as patient coupling member 72 while remaining within the scope of the present invention. Patient coupling member 72 (i.e., the cushion) is fluidly coupled to a rigid support structure 74 which in turn is coupled to elbow conduit 76. Elbow conduit 76 is structured to be coupled to a delivery conduit (not shown) which is in fluid communication with a pressure generating device (also not shown) that is structured to generate a flow of breathing gas which is delivered to the patient through patient coupling member 72.

Support structure 74 includes a base portion 78 having a post portion 80 extending therefrom. In addition, post portion 80 has a pair of posts 82 extending from opposites side thereof. Support structure 74 further includes a pair of extension members 84 extending from opposites side thereof, wherein each extension member 84 includes a loop 86 which is structured to receive a respective lower headgear strap of a headgear assembly (not shown) for securing patient interface device 70 to the head of the patient.

Patient interface device 70 further includes a forehead support 88 that includes forehead cushion 90 that is coupled to support frame 92. Forehead support 88 is structured to provide additional support for patient interface device 70 by engaging the forehead of the patient. Support frame 92 includes loops 94 provided at opposite ends thereof. Each loop 94 is structured to receive a respective upper headgear strap of a headgear assembly (not shown) for securing patient interface device 70 to the head of the patient. Support frame 92 is pivotably coupled to upper end 96 of a support arm 98. The present invention contemplates that the forehead support can have any configuration. For example, the length of support arm 98 can be made adjustable. Also, the forehead cushion can include one or more cushions having any suitable configuration. Also, headgear attaching elements in addition to or other than loops 94 can be provided on the forehead support.

A lower end 100 of support arm 98 includes a loop portion 102 that is structured to receive therethrough post portion 80 of support structure 74, as shown in FIG. 4. In addition, prior to loop portion 102 being inserted over post portion 80 as just described, cam wheel 42' according to an alternative embodiment shown in FIGS. 6A-6E, is inserted over post portion 80 such that post portion 80 is received through central bore 44 of cam wheel 42'. Cam wheel 42' is similar to cam wheel 42, and like parts are labeled with like reference numerals. However, as seen in FIGS. 6A-6E, interior wall 60 of cam wheel 42' includes notches 62, 64 for providing clearance for post 82 as cam wheel 42' is slid over post portion 80. The bottom edge of cam wheel 42 then rests against base portion 78, and cam wheel is permitted to rotate about post portion 80. In addition, post portion 80 is received through loop portion 102, each post 82 is received and held within a respective aperture 104 provided on opposite sides of loop portion 102 such that loop portion 102 and support arm 98 are able to pivot about the axis defined by posts 82. Also, cam wheel is held in place between lower end 100 of support arm 98 and base portion 78 as a result of the engagement between loop portion 102 and post portion 80.

As shown in FIG. 4, lower end 100 of support arm 98 will always contact cam wheel 42' in two places as cam wheel 42' is rotated about post portion 80. Thus, in operation, when a patient dons patient interface device 70, patient coupling member 72 will engage the patient's face and forehead support 88 will engage the patient's forehead. As the patient selectively rotates cam wheel 42 about post portion 80, the varying height of the walls of cam wheel 42' as defined by left and right outside walls 52, 54 and the two points of contact between cam wheel 42 and lower end 100 of support arm 98 described above will support arm 98 to pivot about the axis through that is defined by posts 82. Such pivoting causes forehead support 88 to move inwardly and outwardly along a defined path of movement in a corresponding fashion so that it may readily and easily be adjusted by the patient relative to patient coupling member 72. Thus, support arm 98 serves as a pivot arm that is pivotably coupled to support structure 74.

Figure 5:
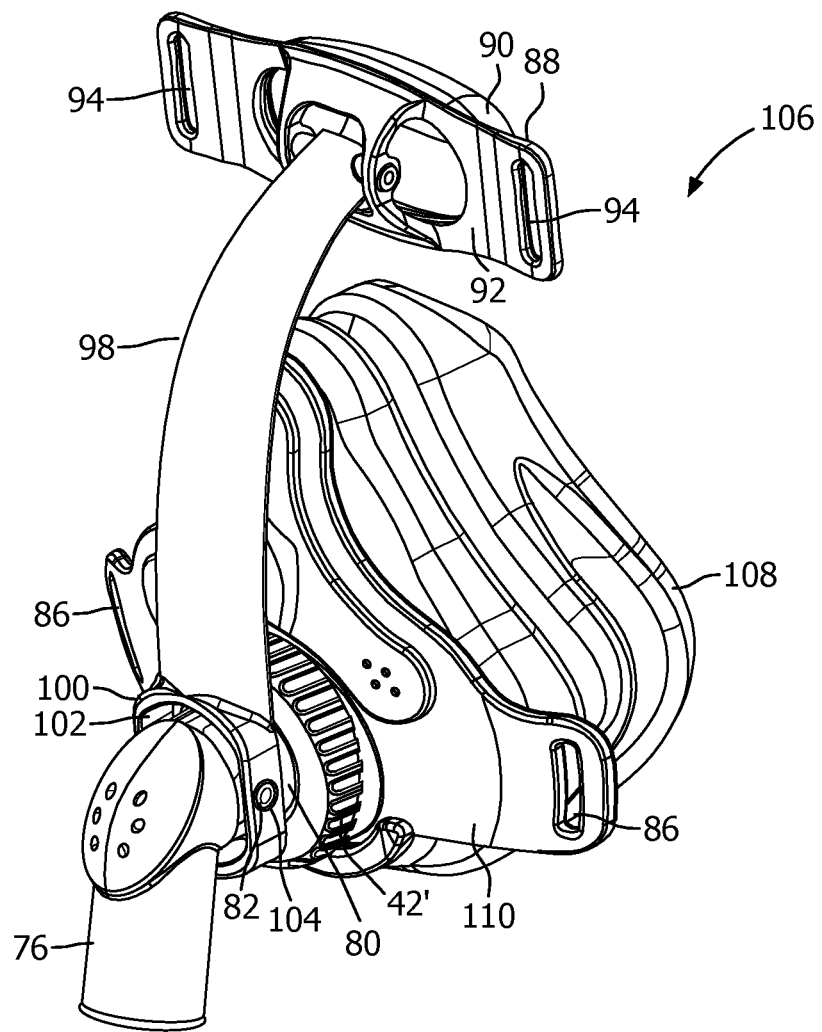
FIG. 5 is an isometric view of a patient interface device according to a further alternative exemplary embodiment of the present invention.
Figure 6A:
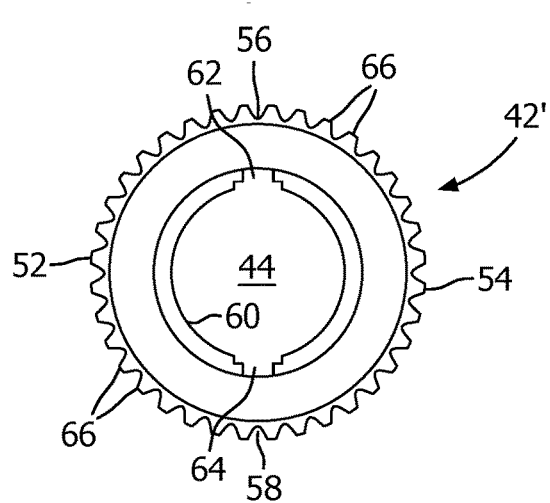
FIGS. 6A-6E are top plan, bottom plan, right side elevational, top side elevational, and isometric views, respectively, of a cam wheel forming part of the patient interface device of FIGS. 4 and 5.
Figure 6B:
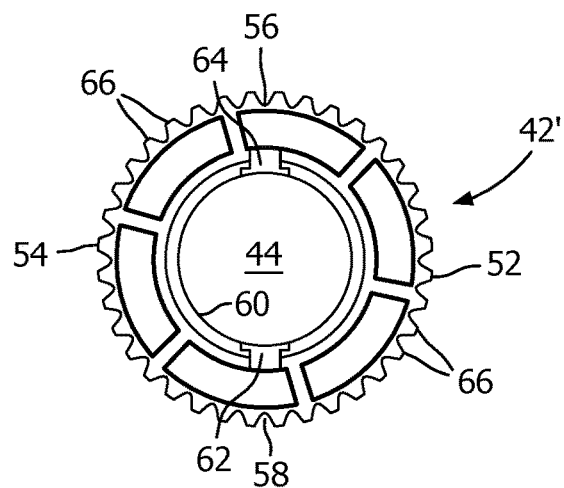
Figure 6C:
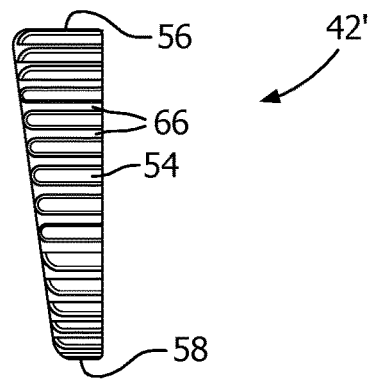
Figure 6D:
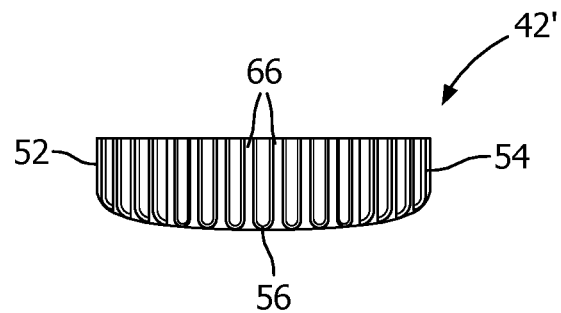
Figure 6E:
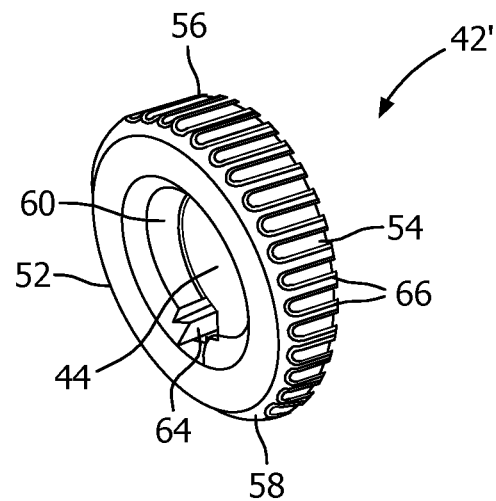

It can be appreciated that rotation of cam wheel 42' results in movement of forehead support 88 relative to patient coupling member. In this embodiment, support structure 12 is fixed on the user's head. As a result, when the cam wheel is actuated the patient coupling member moves toward or away from the user's face, thus adjusting the force of the seal provided by the patient coupling member against the face of the user FIG. 5 is an isometric view of a patient interface device 106 according to an alternative exemplary embodiment of the present invention. Patient interface device is similar to patient interface device 70, and like components are labeled with like reference numerals. Patient interface device 106, however, includes patient coupling member 108, which is a nasal/oral mask that covers the nose and mouth, and alternative rigid support structure 110 to which patient coupling member 108 is fluidly coupled.

Figure 7:
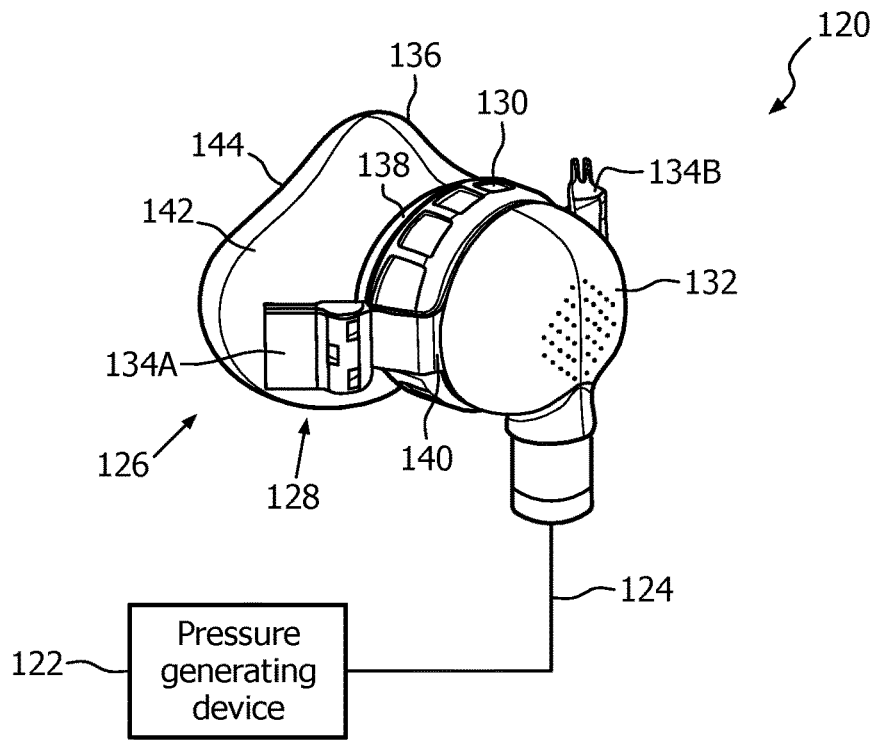
FIGS. 7 and 8 are schematic diagrams of a system adapted to provide a regimen of respiratory therapy to a patient according to another exemplary embodiment.

A system 120 adapted to provide a regimen of respiratory therapy to a patient according to another exemplary embodiment is generally shown in FIGS. 7 (isometric view) and 8 (side view). System 120 includes a pressure generating device 122, a delivery conduit 124, and a patient interface device 126. Pressure generating device 122 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 124 is structured to communicate the flow of breathing gas from pressure generating device 122 to patient interface device 126. Delivery conduit 124 and patient interface device 126 are often collectively referred to as a patient circuit.

Figure 8:
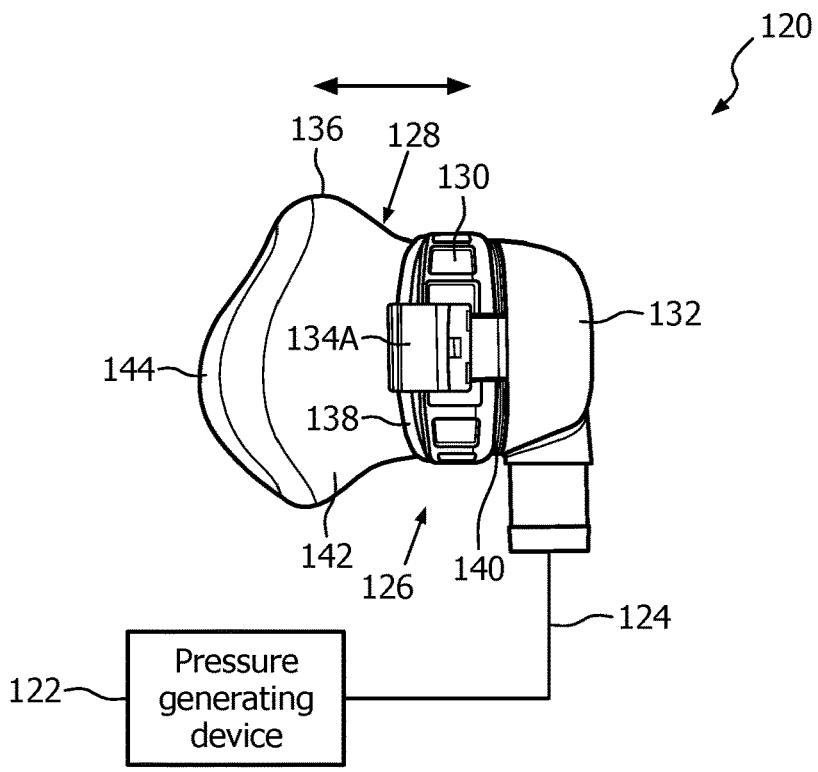

As seen in FIGS. 7 and 8, in the exemplary embodiment, patient interface 126 includes a cushion assembly 128, which in the illustrated embodiment is a nasal mask structured to fit over the nose and of the patient 1. However, other types of cushion assemblies, such as, without limitation, a nasal/oral mask or a nasal cushion, which facilitate the delivery of the flow of breathing gas to the airway of a patient, may be substituted for cushion assembly 128 while remaining within the scope of the present invention. Patient interface 126 further includes a cam wheel 130, a fluid coupling conduit 132, and headgear clips 134A, 134B. Cushion assembly 128, cam wheel 130, fluid coupling conduit 132, and headgear clips 134A, 134B are each described in greater detail below. It can be appreciated that this embodiment differs from the previous embodiment in FIGS. 4 and 5, in that the forehead support has been omitted.

Figure 9:
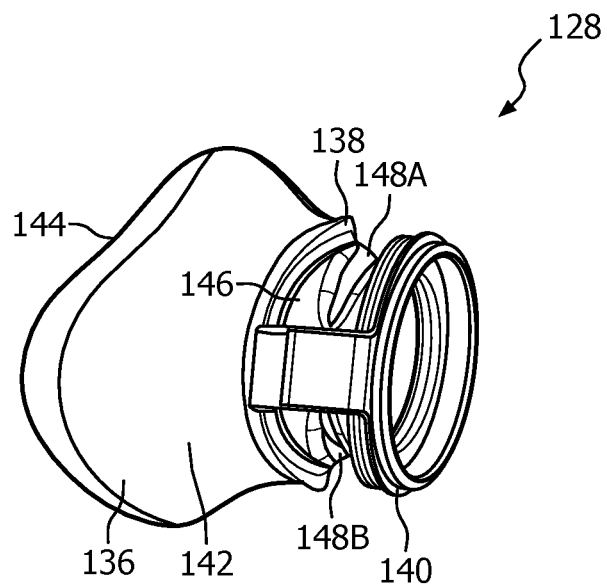
FIG. 9 is an isometric view of a cushion assembly forming a part of a patient interface device of the system of FIGS. 7 and 8 according to the exemplary embodiment.

FIG. 9 is an isometric view of cushion assembly 128 according to the exemplary embodiment. Cushion assembly 128 includes a cushion member 136 having a ring member 138 and a frame member 140 coupled thereto.

Figure 10:
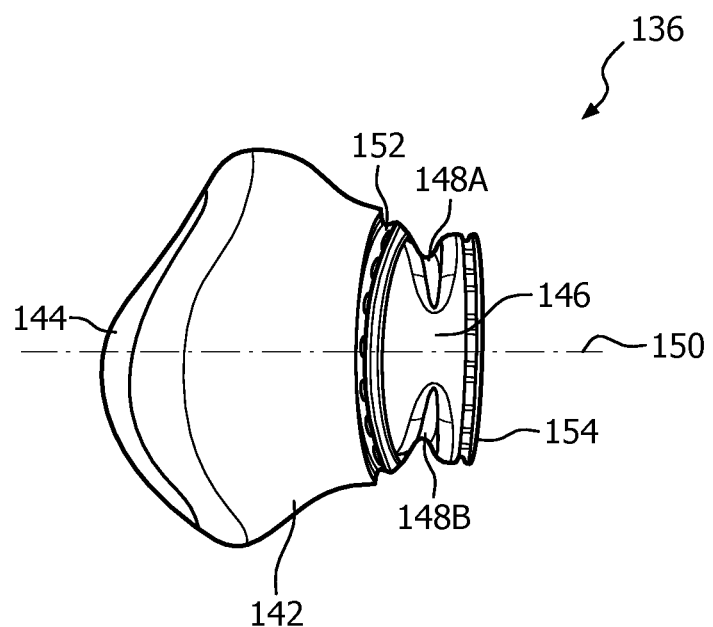
FIG. 10 is a side elevational view of a cushion member forming a part of the cushion assembly of FIG. 9.

FIG. 10 is a side elevational view of cushion member 136. Cushion member 136 is defined from a unitary piece of soft, flexible, cushiony, elastomeric material, such as, without limitation, silicone, an appropriately soft thermoplastic elastomer, closed cell foam, or any combination of such materials. As seen in FIGS. 9 and 10, cushion member 136 includes a main body portion 142 defining a chamber for receiving breathing gasses and having a patient sealing surface 144 structured to engage the face of a patient. Cushion member 136 also includes a bellows portion 146 adjacent to main body portion main body portion 142. Bellows portion 146 includes pleats 148A and 148B and is structured to be extendible along the longitudinal axis 150 of cushion member 136 in the manner described elsewhere herein.

In the exemplary embodiment, cushion assembly 128 is formed by overmolding cushion member 136 onto ring member 138 and frame member 140. In particular, as a result of such a process, ring member 138 is positioned at a junction 152 of main body portion 142 and bellows portion 148 of cushion member 136, and frame member 140 is positioned at a distal end 154 of bellows section 146 that is fluidly coupled to fluid coupling conduit 132.

Figure 11A:
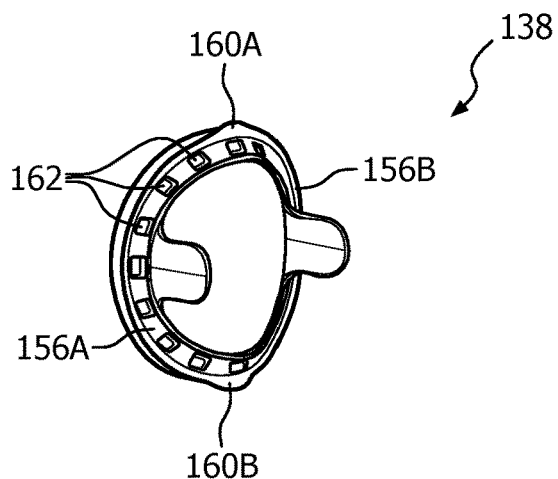
FIGS. 11A, 11B and 11C are an isometric view, a side elevational view and a top plan view, respectively, of a ring member forming a part of the cushion assembly of FIG. 9.
Figure 11B:
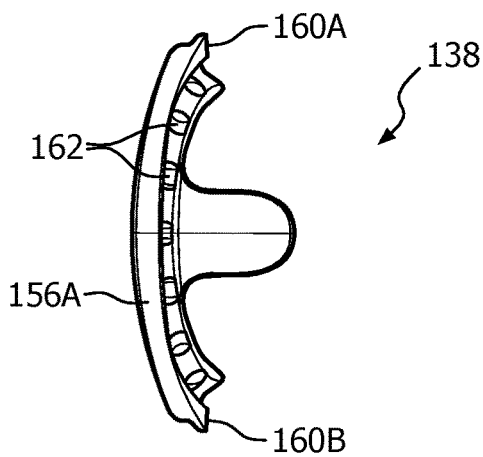
Figure 11C:
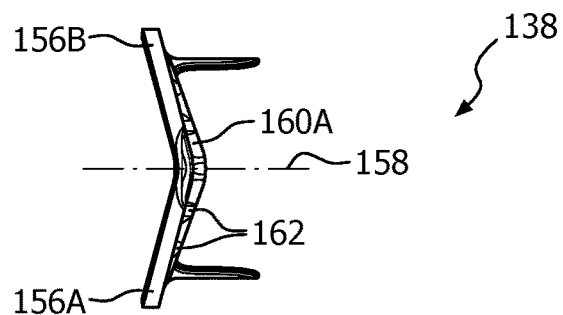

FIGS. 11A, 11B and 11C are an isometric view, a side elevational view and a top plan view, respectively, of ring member 138 according to the exemplary embodiment. Ring member 138 generally has a saddle-like shape and includes a first arcuate member 156A joined to a second arcuate member 156B. As seen best in FIG. 11C, each arcuate member 156A, 156B is configured such that the rear side thereof forms an acute angle with respect to the longitudinal axis 158 thereof. In other words, each arcuate member 156A, 156B is angled/disposed rearwardly with respect to a front side of ring member 138 such that the angle between the rear surfaces of arcuate members 156A and 156B is less than 180 degrees. In addition, frame member 138 includes top and bottom engagement surfaces 160A and 160B, at the junction points of arcuate member 156A, 156B. The function of engagement surfaces 160A and 160B is described elsewhere herein. In addition, ring member 138 has a plurality of orifices 162 for facilitating the overmolding process described above.

Figure 12:
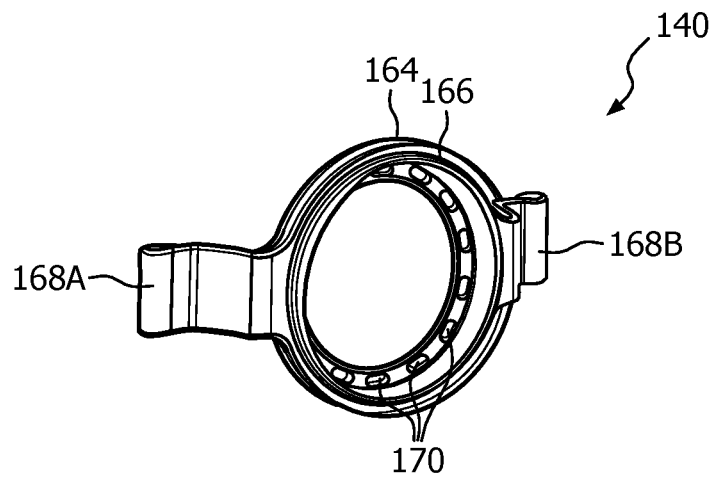
FIG. 12 is an isometric view of a frame member forming a part of the cushion assembly of FIG. 9.

FIG. 12 is an isometric view of frame member 140 according to the exemplary embodiment. Frame member 140 has a main body 164 having a generally annular shape. Main body 164 includes a circumferential ridge member 166 which is structured to enable a fluid tight connection to be made to fluid coupling conduit 132. In addition, frame member 140 includes arms 168A and 168B extending from opposite sides of main body 164. Arms 168A and 168B are structured to receive and hold headgear clips member 134A, 134B, which in turn are structured to be coupled to the straps of a headgear component (not shown) for securing patient interface device 126 to the head of the patient. Finally, frame member 140, like ring member 138, has a plurality of orifices 170 for facilitating the overmolding process described above.

Figure 13A:
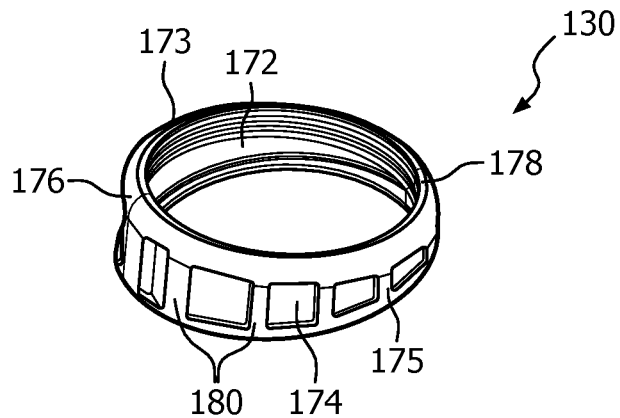
FIGS. 13A-13D show various views of a cam wheel forming a part of a patient interface device of the system of FIGS. 7 and 8 according to the exemplary embodiment.
Figure 13B:
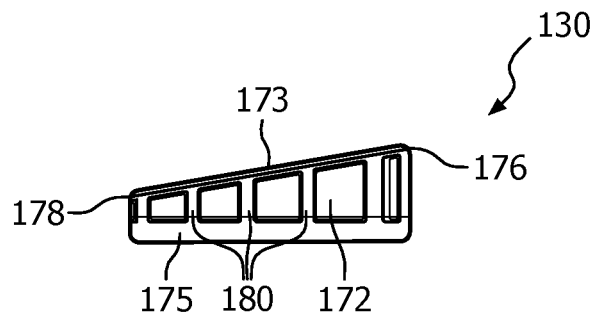
Figure 13C:
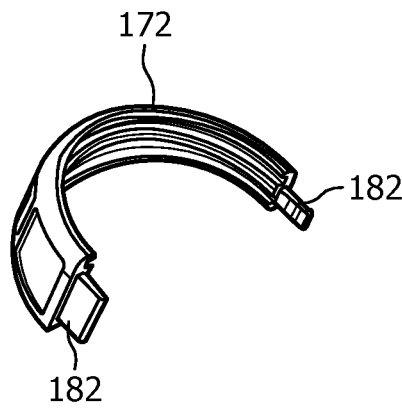
Figure 13D:
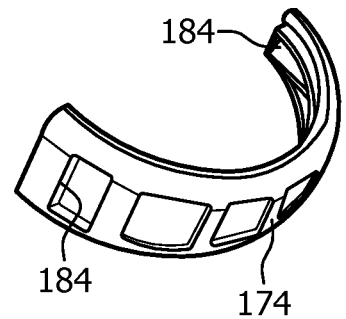

FIGS. 13A and 13B are isometric and side elevational views, respectively, of cam wheel 130 according to the exemplary embodiment. Cam wheel 130 is a cylindrically shaped member having first and second outside walls 172, 174 that define a top surface 173 and a bottom surface 175 of cam wheel 130. As seen in FIGS. 13A and 13B, first and second outside walls 172, 174 vary in height from a maximum at top middle portion 176 of cam wheel 130 to a minimum at bottom middle portion 178 of cam wheel 130. More particularly, in the illustrated embodiment, the height of each of first outside wall 172 and second outside wall 174 tapers and decreases linearly from top middle portion 176 to bottom middle portion 178. First and second outside walls 172, 174 are provided with ridges 180 to facilitate gripping and turning of cam wheel 130 as described elsewhere herein. While a generally linear change in height for the wall of the cam wheel is shown, it is to be understood that the present invention contemplates that the wall of the cam wheel can have other shapes or changes in height. In addition, in the exemplary embodiment, cam wheel 130 is formed in two pieces, shown in FIGS. 13D and 13E, that are then fit together by a suitable mechanism, such as a snap fit, a friction fit or an adhesive. In the exemplary embodiment, first outside wall 172 includes tabs 182 that are structured to be received within slots 184 provided in second outside wall 174.

Figure 14:
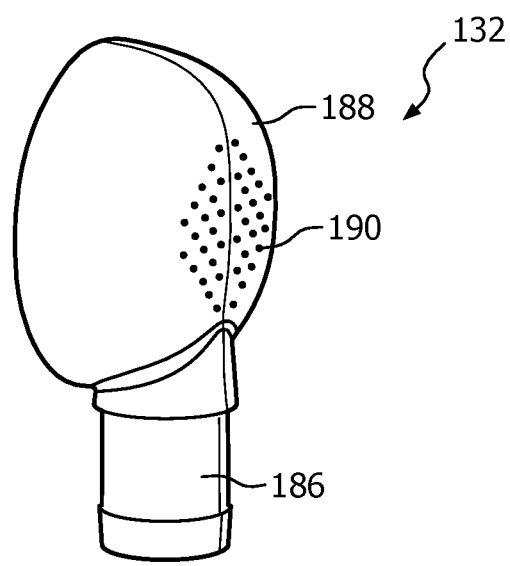
FIG. 14 is an isometric view of a fluid coupling conduit forming a part of a patient interface device of the system of FIGS. 7 and 8 according to the exemplary embodiment.

FIG. 14 is an isometric view of fluid coupling conduit 132. As seen in FIG. 14, fluid coupling conduit 132 includes a cylindrical first connector portion structured to be attached to delivery conduit 124, and a hemispherical second connector portion 188 structured to be attached to cushion assembly 128. Second connector portion 188 defines a chamber having an exhaust port 190 comprising a plurality of orifices for exhausting exhaled gasses to atmosphere.

Figure 15A:
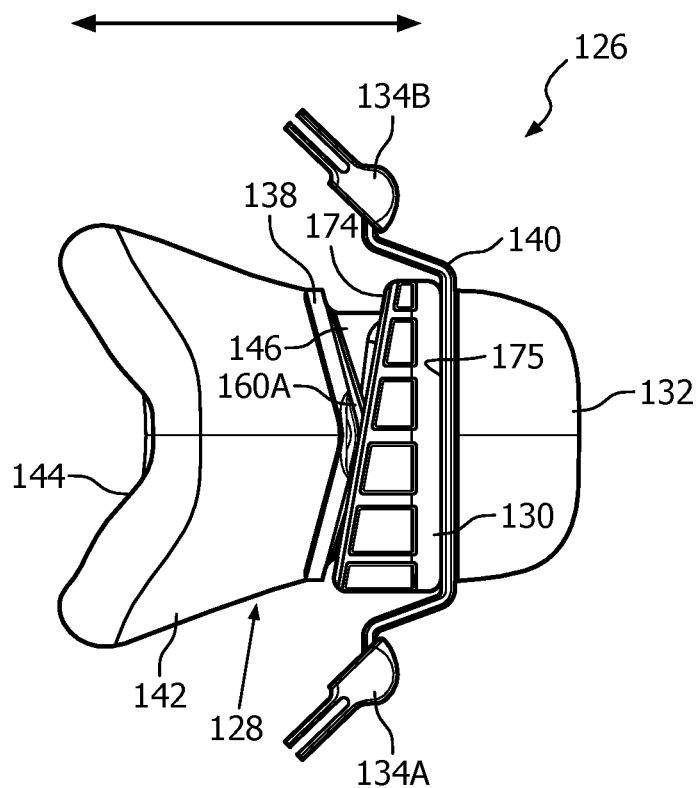
FIGS. 15A and 15B are top and bottom plan views, respectively, of a patient interface device of the system of FIGS. 7 and 8 according to the exemplary embodiment.
Figure 15B:
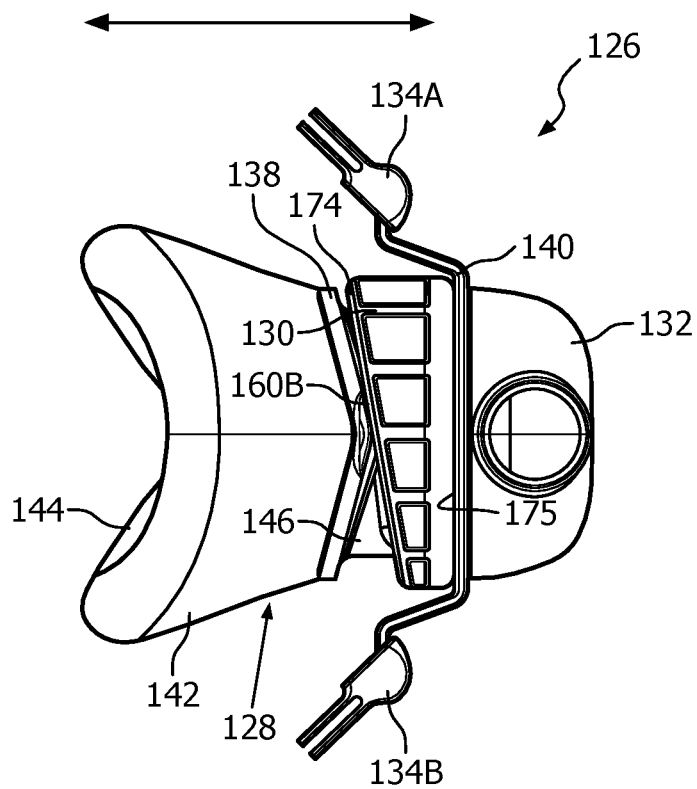

In the exemplary embodiment, patient interface device 126 is thus assembled by snapping cam wheel 130 together as just described over bellows portion 146 of cushion member 136 of cushion assembly 128. Fluid coupling conduit 132 is then attached to circumferential ridge member 166 of frame member 140 as seen in FIGS. 7 and 8 When this is done, cam wheel 130 is able to freely rotate about bellows portion 146. In addition, as shown in FIGS. 15A and 15B, bottom surface 175 of cam wheel 130 will engage the rear of main body 164 of frame member 140, and corresponding, opposite points of top surface 173 will engage top and bottom engagement surfaces 160A and 160B of frame member 138.

In operation, the patient is able to adjust the position of main body portion 142 of cushion assembly 128 (see arrows in FIGS. 8, 15A and 15B) to increase comfort and seal by rotating cam wheel 130. In particular, as cam wheel 130 is rotated relative to bellows portion 146, different points of top surface 173 will engage top and bottom engagement surfaces 160A and 160B of frame member 138, causing pleats 148A and 148B of bellows portion 146 to expand or contract relative to longitudinal axis 150 of cushion member 136 depending on the particular height of first and second outside walls 172, 174 at the then engaging points of top surface 173. As a result, main body portion 142 will move relative to the longitudinal axis 150 of cushion member 136.

Figure 16:
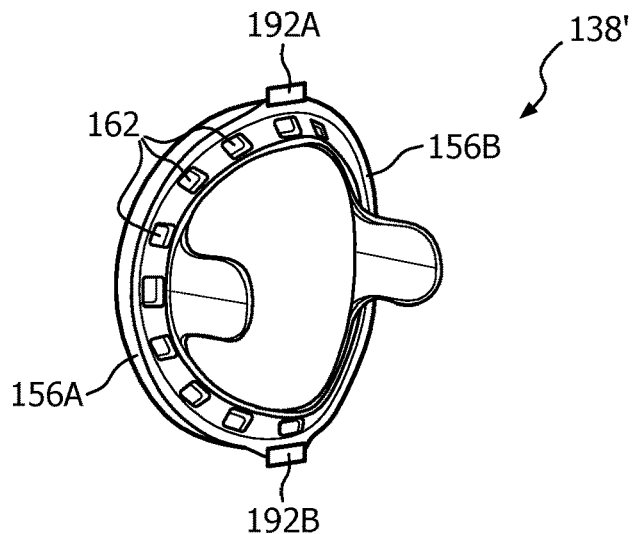
FIG. 16 is an isometric view of an alternative ring member.
Figure 17A:
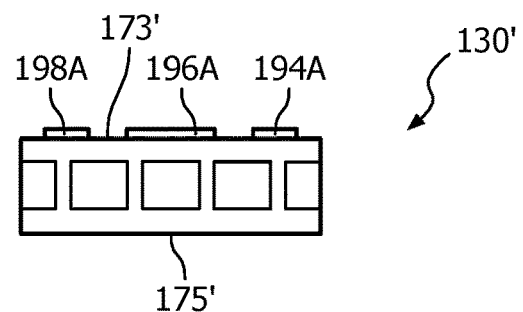
FIGS. 17A and 17B are side elevational and top plan views, respectively, of an alternative cam wheel that may be employed to create a patient interface according to an alternative exemplary embodiment of the invention.
Figure 17B:
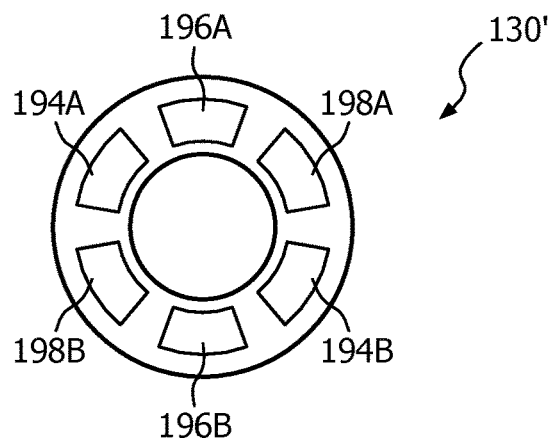

FIG. 16 is an isometric view of an alternative ring member 138', and FIGS. 17A and 17B are side elevational and top plan views, respectively, of an alternative cam wheel 130' that may be employed in place of ring member 138 and cam wheel 130 to create a patient interface according to an alternative exemplary embodiment of the invention. Ring member 138' is similar to ring member 138, and like portions are labeled with like reference numerals. However, as seen in FIG. 16, ring member 138' differs in that it includes first permanent magnet members 192A, 192B having a first polarity at the junction points of arcuate member 156A, 156B (i.e., the locations of top and bottom engagement surfaces 160A and 160B in ring member 138). In addition, cam wheel 130' is a cylindrically shaped member having outside walls that define a top surface 173' and a bottom surface 175' of cam wheel 130'. As seen in FIG. 17A, the outside walls of cam wheel 130' do not vary in height. In addition, a plurality of permanent magnet members are provided on top surface 173'. In particular, those magnet members all have a second polarity that is opposite the first polarity of magnet members 192A, 192B, and include first magnet members 194A, 194B located opposite one another and having a first strength, second magnet members 196A, 196B located opposite one another and having a second strength greater than the first strength, and third magnet members 198A, 198B located opposite one another and having a third strength greater than the second strength. Alternatively, the permanent magnet members provided on top surface 173' may have different sizes to yield different magnetic opposing forces.

In operation, when ring member 138' and cam wheel 130' are employed in place of ring member 138 and cam wheel 130 to create a patient interface similar to patient interface 126, the patient is able to adjust the position of main body portion 142 of cushion assembly 128 to increase comfort and seal by rotating cam wheel 130'. In particular, as cam wheel 130' is rotated relative to bellows portion 146, different pairs of magnet members 194A, 194B, 196A, 196B, and 198A, 198B will be positioned adjacent magnet members 192A, 192B of ring member 138' to provide an opposing force with respect thereto (based on the opposite polarity of the magnet members). The opposing magnetic forces will cause pleats 148A and 148B of bellows portion 146 to expand or contract relative to longitudinal axis 150 of cushion member 136 to a certain degree (i.e., a certain amount) depending on the strength (or size) of the pairs of magnet members 194A, 194B, 196A, 196B, and 198A, 198B that are then adjacent to and therefore opposing magnet members 192A, 192B of ring member 138'. As a result, main body portion 142 will move relative to the longitudinal axis 150 of cushion member 136 (by an amount determined by the particular opposing magnets).

In the embodiments described above, rotating the cam wheel causes the patient coupling member to move or flex in a direction that causes the cushion to move in a longitudinal direction, i.e., to move generally in-line with a centerline of the user. This allows the user, for example, to adjust the pressure applied by cushion at the bridge of the nose. The present invention also contemplate moving the patient coupling member in other directions, such as laterally, using the cam wheel or using multiple cam wheels. In addition, other adjustment mechanisms can be provided with the patient interface device.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a cushion member having a main body portion having a surface structured to engage a face of a patient;
   a frame member coupled to the cushion member, the frame member being structured to be coupled to a headgear;
   a fluid coupling conduit coupled to a first side of the frame member;
   an engagement member coupled to the cushion member; and
   a rotatable cam wheel disposed between a second side of the frame member and the engagement member, wherein a first surface of the cam wheel engages the engagement member such that rotation of the cam wheel relative to the cushion member changes a position of the main body portion relative to the frame member, wherein rotation of the cam wheel relative to the cushion member moves the main body portion relative to the frame member along a longitudinal axis of the cushion member, wherein the cushion member includes a flexible portion adjacent the main body portion, wherein the cam wheel is rotatable about the flexible portion, and wherein rotation of the cam wheel about the flexible portion causes the flexible portion to deflect thereby moving the cushion member relative to the frame member.

2. The patient interface device according to claim 1, wherein the flexible portion includes a pleat that is expandable along the longitudinal axis of the cushion member.

3. The patient interface device according to claim 1, wherein the engagement member comprises a ring member surrounding the cushion member at an end of the man body portion opposite the surface structured to engage the face of the patient, and wherein the engagement member continuously engages the cam wheel at only two locations on the first surface of the cam wheel as the cam wheel is rotated.

4. The patient interface device according to claim 3, wherein the engagement member includes a first engagement surface location and a second engagement surface location that engage the cam wheel at the two locations.

5. The patient interface device according to claim 4, wherein the first engagement surface location and the second engagement surface location are located directly opposite one another about a perimeter of the engagement member.

6. The patient interface device according to claim 4, wherein the ring member generally has a saddle-like shape and includes a first arcuate member and a second arcuate member joined to one another at the first and second engagement surface locations.

7. The patient interface device according to claim 6, wherein the first arcuate member and the second arcuate member are each disposed rearwardly with respect to a front side of the ring member such that an angle between respective rear surfaces of the first arcuate member and the second arcuate member is less than 180 degrees.

8. The patient interface device according to claim 3, wherein the cam wheel wraps around the flexible portion, wherein the cam wheel has first and second outside walls, wherein both the first outside wall and the second outside wall vary in height from a maximum at a top middle portion of the cam wheel to a minimum at a bottom middle portion of the cam wheel.

9. The patient interface device according to claim 8, wherein the height of each of the first outside wall and the second outside wall tapers and decreases linearly from the top middle portion to the bottom middle portion.

10. The patient interface device according to claim 1, wherein the frame member has a first arm having a first headgear clip attached thereto and a second arm having a second headgear clip attached thereto.

11. A patient interface device, comprising:
    a cushion member having a main body portion having a surface structured to engage a face of a patient;
    a frame member coupled to the cushion member, the frame member being structured to be coupled to a headgear;
    a fluid coupling conduit coupled to a first side of the frame member;
    one or more first magnets coupled to the cushion member, the one or more first magnets having a first polarity; and
    a rotatable cam wheel disposed between a second side of the frame member and the one or more first magnets, the cam wheel including one or more second magnets facing toward the one or more first magnets and having a second polarity opposite the first polarity, wherein rotation of the cam wheel relative to the cushion member changes a position of the main body portion relative to the frame member as a result of opposing forces between the one or more first magnets and one or more of the plurality of second magnets.

12. The patient interface device according to claim 11, wherein the one or more second magnets comprise a plurality of second magnets having different strengths or sizes.

13. The patient interface device according to claim 11, wherein the one or more first magnets are provided on a ring member coupled to the cushion member.

14. The patient interface device according to claim 11, wherein rotation of the cam wheel relative to the cushion member moves the main body portion relative to the frame member along a longitudinal axis of the cushion member.

* * * * *